United States Patent [19]

Nakagawa et al.

[11] Patent Number: 5,646,292

[45] Date of Patent: Jul. 8, 1997

[54] BLOWING AGENTS OF TETRAZOLES AND THEIR DERIVATIVES

[75] Inventors: Satoshi Nakagawa, Himeji; Hideki Ogawa, Takasago; Hiroaki Tanaka, Takasago; Atsuhiro Onishi, Takasago, all of Japan

[73] Assignee: Toyo Kasei Kogyo Company Limited, Osaka, Japan

[21] Appl. No.: 643,357

[22] Filed: May 6, 1996

[30] Foreign Application Priority Data

Jun. 9, 1995 [JP] Japan ................................. 7-168215

[51] Int. Cl.$^6$ ................................................. C07D 257/06
[52] U.S. Cl. .................................................... 548/251
[58] Field of Search .......................... 548/251; 546/268.4

[56] References Cited

U.S. PATENT DOCUMENTS

| | | | |
|---|---|---|---|
| 4,142,029 | 2/1979 | Illy | 548/251 |
| 4,404,214 | 9/1983 | Takeda et al. | 546/268.4 |
| 4,871,864 | 10/1989 | Daum et al. | 549/60 |
| 4,921,965 | 5/1990 | Rothgery et al. | 548/251 |
| 4,948,439 | 8/1990 | Poole et al. | 149/46 |
| 5,035,757 | 7/1991 | Poole | 149/46 |

*Primary Examiner*—Jacqueline Haley
*Attorney, Agent, or Firm*—Wenderoth, Lind & Ponack

[57] ABSTRACT

Disclosed is a novel blowing agent of tetrazoles and their derivatives. The blowing agent comprising tetrazole derivatives is harmless, odorless and inexpensive. Moreover, the agent is low in physical sensitivities and safe in use, and generates clean gas by being sharply decomposed only due to temperature. The blowing agent of tetrazoles and their derivatives employs aminotetrazole derivatives represented by the general formula (1). The blowing agent offers foaming agents for resin molded bodies having good thermal properties, inflators for air bags serving as automobile safety protection, or smoking agents for diffusing chemicals by a low-cost inexpensive synthetic process.

5 Claims, No Drawings

BLOWING AGENTS OF TETRAZOLES AND THEIR DERIVATIVES

BACKGROUND OF THE INVENTION

(1) Field of the Invention

This invention relates to blowing agents of tetrazoles and their derivatives which are used as foaming agents for precision molding of resins or reducing the weight of resin molded products, inflators for automobile air bags, or smoking agents for effectively diffusing agricultural chemicals such as insecticides and bactericides, or chemicals such as anti-contamination agents and aromatizing agents.

(2) Description of the Prior Art

Since crystalline resins, of course, crystallize and shrink during cooling steps after molding, it has been difficult to obtain a molded body having the same precise dimensions as its mold base. This apparent shrinkage in precision molding has been avoided by experimentally adjusting the size of the mold base. However, it has been difficult to obtain molded bodies with complete precision by the conventional processes. To prevent the molded bodies from shrinking, pneumatic pressure was applied into the core portion of the molded bodies (Japanese Patent Publications SHO 48-41264, SHO 57-14968) or an addition of more expensive foaming agents was proposed (Japanese Patent Laid-Open Publications SHO 50-129563, SHO 53-12864, SHO 56-61435, and U.S. Pat. No. 4,871,861). In the latter case, however, there have been available no satisfactory foaming agents for thermoplastic resins having high melting points, and therefore there have been no quality high foaming molded products.

Also, conventionally, sodium azide has been used as the inflator for air bags for automobile safety protection. Since sodium azide has a problem of toxicity, blowing agents of tetrazoles and their derivatives have been proposed as a countermeasure for the toxicity (Japanese Patent Laid-Open Publication SHO 46-906, DE 2,150,465, Japanese Patent Laid-Open Publications SHO 49-87583, SHO 50-75592, SHO 57-123885, SHO 57-123886, HEI 2-225159, HEI 2-184590, U.S. Pat. No. 4,948,439, Japanese Patent Laid-Open Publications HEI 2-221179, HEI 2-225389, and U.S. Pat. No. 5,035,757).

SUMMARY OF THE INVENTION

The conventional blowing agents of tetrazoles and their derivatives have had such problems as sublimation at low temperatures, or high physical sensitivities like friction sensitivity and falling weight sensitivity, which leads to lack of safety in working conditions or equipments for treating them. Moreover, there has been another problem that the conventional blowing agents of tetrazoles and their derivatives are more expensive than sodium azide. Although it is essential that the smoking agent should be harmless to human and mammals as well as odorless, the conventionally used smoking agents have been insufficient to meet these requirements. The object of this invention is to provide novel blowing agents of tetrazoles and their derivatives that are harmless and odorless, inexpensive and low in physical sensitivities such as frictional sensitivity or falling weight sensitivity, and safe in their treatment, and that definitely decompose only due to temperature, and blow a clean gas.

DETAILED DESCRIPTION OF THE INVENTION

In a first aspect of the present invention, the invention provides a blowing agent comprising aminotetrazole derivatives represented by the following general formula (1):

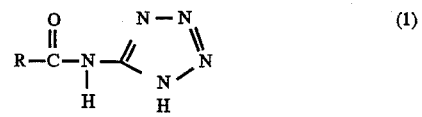

(wherein R represents $CH_3-$, $CH_3CH_2-$, $CH_3(CH_2)_2-$, $CH_3(CH_2)_3CH(CH_2CH_3)CH_2-$.

In a second aspect of the present invention, the invention provides a blowing agent of tetrazoles and their derivatives according to the first aspect, wherein the tetrazole derivatives are used as foaming agents for molded bodies of resins, inflators for automobile safety air bags, or smoking agents for diffusing various types of chemicals.

The object of this invention is to provide blowing agents having better performance than that of 5-aminotetrazole, by replacing R in the general formula (1) with $CH_3-$, $CH_3CH_2-$, $CH_3(CH_2)_2-$, or $CH_3(CH_2)_2CH(CH_2CH_3)CH_2-$. For the process of synthesizing the tetrazole derivatives with lower cost, readily and in better yield, acid anhydrides or organic acid chlorides corresponding to the R group were selected as reaction agents.

The tetrazole derivatives according to this invention can be synthesized by conventional processes. In a typical example, an organic acid anhydride that serves as both a solvent and a starting material is used in large excess for the reaction with the organic acid anhydride. With 5-aminotetrazole added to the organic acid anhydride, the mixture is allowed to react under stirring at a reaction temperature of several tens degree centigrade for several hours, by which the desired product is obtained. The crystalline product is filtered off from the organic acid anhydride as a solvent. When an organic acid chloride is used, 5-aminotetrazole is dissolved in a soluble liquid, for example, DMF (dimethylformamide), and a chemical equivalence of the organic acid chloride is added to the solution. Then, the reaction completes immediately to give the desired product. The crystalline product is filtered off and, if necessary, purified by recrystallization.

EXAMPLES

Example 1

In a 500 ml four-necked flask equipped with a condenser, a thermometer and a stirrer, 18 g (0.212 mole) of 5-aminotetrazole was measured, followed by adding 300 ml of acetic anhydride, and the mixture was heated at 70° C. in an oil bath. The reaction was continued for 3 hours. Acetamide of 5-aminotetrazole (formula 3) was precipitated as crystals. After cooling, the crystals were filtered off and dried at 100° C. under reduced pressure overnight. Thus, 25.5 g of white crystals (where the yield based on 5-aminotetrazole was 95%) was obtained.

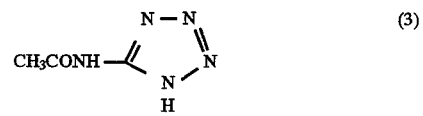

Example 2

Propyonmide (formula 4-1) or butylmide (formula 4-2) of 5-aminotetrazole was able to be quantitatively obtained by allowing corresponding propyonic anhydride and butylic anhydride to react with 5-aminotetrazole, respectively, under the same reaction conditions as in Example 1.

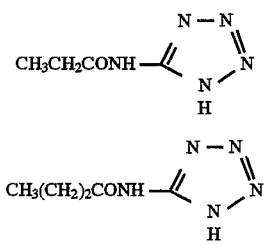

Example 3

An example of the synthetic process using an acid chloride as a starting material is shown below:

N-[1H-tetrazole-5-yl]-N-valeramide (Mw: 120.58)

In a 500 ml four-necked flask equipped with a stirrer, 17.641 g (0.207 mole) of 5-aminotetrazole was measured and, after adding 300 ml of DMF, the material was dissolved under stirring. Then, 20.98 g (0.207 mole) of trlethylamine was added. Into this solution, 25 g (0.207 mole) of valeroyl chloride was added dropwise from a dropping funnel under stirring at room temperature. Immediately after the addition, the solution became cloudy with the white precipitates of the by-product, triethylamine hydrochloride, and the reaction temperature of the solution increased to about 50° C. or more. The solution was cooled in an ice bath to room temperature and allowed to stand for 1 hour under stirring. The solution was then poured into a 1 litter beaker filled with a twofold volume of water to DMF, and the mixed solution was stirred vigorously for about 1 hour to dissolve triethylamine hydrochloride. The crystals of the desired product precipitated were washed with a twofold volume of water and filtered off. The crystals were dried at room temperature, followed by drying at 100° C. overnight under a reduced pressure. White opaque fine powder (formula 5), 19.1 g, was obtained (where yield of N-[1H-tetrazole-5-yl]-N-valleramide was 54.5% based on 5-aminotetrazole). Melting points and decomposition temperatures, as determined by differential thermal analysis, of the aminotetrazole derivatives obtained in Examples 1 to 3 according to this invention are listed in Table 1.

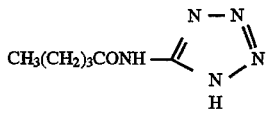

TABLE 1

Melting point and decomposition temperature of

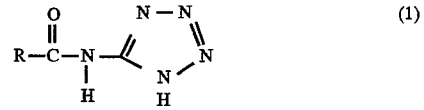

| R | Melting point °C. | Decomposition temperature |
|---|---|---|
| $CH_3-$ | 266 | 278 (sharp) |
| $CH_3CH_2-$ | | 284 (sharp) |
| $CH_3(CH_2)_2-$ | | 273 (sharp) |
| $CH_3(CH_2)_3CH$ $(CH_2CH_3)CH_2-$ | | 255 |

EFFECT OF THE INVENTION

This invention makes it possible to provide tetrazole derivatives having good thermal properties through a low-cost synthetic process. The tetrazole derivatives have greater effects and more safety, compared with conventional products, for use as foaming agents for molded bodies of synthetic resins, inflators for air bags serving as automobile safety protection, or smoking agents for diffusing various chemicals.

What we claim is:

1. Aminotetrazole derivatives represented by the following general formula (1):

wherein R represents $CH_3-$, $CH_3CH_2-$ $CH_3(CH_2)_2-$, or $CH_3(CH_2)_3CH(CH_2CH_3)CH_2-$.

2. An aminotetrazole derivative according to claim 1 wherein R is $CH_3-$.

3. An aminotetrazole derivative according to claim 1 wherein R is $CH_3CH_2-$.

4. An aminotetrazole derivative according to claim 1 wherein R is $CH_3(CH_2)_2$.

5. An aminotetrazole derivative according to claim 1 wherein R is $CH_3(CH_2)_3CH(CH_2CH_3)CH_2$.

* * * * *